(12) United States Patent
Camenisch et al.

(10) Patent No.: US 9,723,832 B2
(45) Date of Patent: Aug. 8, 2017

(54) MODULAR SAMPLE STORE

(75) Inventors: Johann Camenisch, Chur (CH); Beat Reuteler, Butzberg (CH); Mirko Hebenstreit, Jettingen-Sheppach (DE); Jurg Tanner, Ittigen (CH); Christian Cachelin, Saviese (CH)

(73) Assignee: Brooks Automation, Inc., Chelmsford, MA (US)

( * ) Notice: Subject to any disclaimer, the term of this patent is extended or adjusted under 35 U.S.C. 154(b) by 304 days.

(21) Appl. No.: 13/501,890

(22) PCT Filed: Oct. 19, 2009

(86) PCT No.: PCT/EP2009/063684
§ 371 (c)(1),
(2), (4) Date: Sep. 26, 2012

(87) PCT Pub. No.: WO2011/047710
PCT Pub. Date: Apr. 28, 2011

(65) Prior Publication Data
US 2013/0011226 A1     Jan. 10, 2013

(51) Int. Cl.
*B65G 1/04* (2006.01)
*B65G 65/00* (2006.01)
(Continued)

(52) U.S. Cl.
CPC .............. *A01N 1/0263* (2013.01); *A47F 5/00* (2013.01); *B65G 1/0464* (2013.01); *B65G 1/06* (2013.01);
(Continued)

(58) Field of Classification Search
CPC ........... F25D 13/04; F25D 13/06; G01N 1/42; G01N 2035/00445; A01N 1/0252
See application file for complete search history.

(56) References Cited

U.S. PATENT DOCUMENTS 2,165,513 A    7/1939   Smith
6,357,983 B1   3/2002   Junca
(Continued)

FOREIGN PATENT DOCUMENTS

EP    0904841 A2    3/1999
EP    0925333 A1    6/1999
(Continued)

OTHER PUBLICATIONS

International Search Report dated Jan. 25, 2011.
(Continued)

*Primary Examiner* — P. Kathryn Wright
(74) *Attorney, Agent, or Firm* — Perman & Green, LLP; Colin C. Durham

(57) ABSTRACT

A modular sample store including a storage area; a service area; a transfer area; a motorized robot with a lifting device and at least one platform; and a controller. The sample store service area includes one integrally formed cubic vat module and the sample store storage area includes at least one integrally formed cubic vat module. Each one of the aforementioned vat modules includes an essentially horizontal vat floor and four joining vat walls that are connected to the vat floor and that are leaving an open vat space. The modular sample store also includes upper side walls and a cover plate to close the sample store. Each vat floor and vat wall includes an outside liner and an inside liner, which outside and inside liners in each case are separated by a clearance. This clearance is essentially filled with a polymer foam material that provides fixation of the outside and inside liners to each other as well as thermal insulation of and reinforcement to the thus integrally formed cubic vat module sandwich construction.

12 Claims, 8 Drawing Sheets

(51) Int. Cl.
  *A01N 1/02*   (2006.01)
  *G01N 35/00*  (2006.01)
  *G01N 35/10*  (2006.01)
  *A47F 5/00*   (2006.01)
  *B65G 1/06*   (2006.01)

(52) U.S. Cl.
  CPC ..... *G01N 35/0099* (2013.01); *G01N 35/1095* (2013.01); *G01N 2035/00326* (2013.01); *G01N 2035/00435* (2013.01); *G01N 2035/00445* (2013.01); *Y10T 29/49826* (2015.01)

(56) References Cited

U.S. PATENT DOCUMENTS

| | | | |
|---|---|---|---|
| 6,694,767 | B2 | 2/2004 | Junca |
| 7,858,032 | B2 | 12/2010 | Le Comte et al. |
| 2004/0141882 | A1 | 7/2004 | Mimura et al. |
| 2008/0260511 | A1* | 10/2008 | Fattinger et al. .......... 414/788.1 |
| 2012/0060539 | A1* | 3/2012 | Hunt et al. ................. 62/336 |
| 2012/0134898 | A1* | 5/2012 | Malin ......................... 422/559 |

FOREIGN PATENT DOCUMENTS

| | | |
|---|---|---|
| EP | 1391402 A2 | 2/2004 |
| EP | 1895307 A1 | 3/2008 |
| EP | 1939561 A2 | 7/2008 |
| EP | 1975626 A1 | 10/2008 |
| FR | 2888328 A1 | 1/2007 |
| JP | 06390768 | 4/1988 |
| JP | 02125739 | 10/1990 |
| JP | 2003058611 | 2/2003 |
| JP | 2004131249 A | 4/2004 |
| JP | 2006347773 | 12/2006 |
| JP | 2007529733 | 10/2007 |
| JP | 2008169042 | 7/2008 |

OTHER PUBLICATIONS

International Preliminary Report on Patentability Application PCT/EP2010/065656 dated Apr. 24, 2012.
International Preliminary Report on Patentability Application PCT/EP2009/063684 dated Mar. 26, 2012.
International Search Report dated Jul. 6, 2010.

* cited by examiner

MODULAR SAMPLE STORE

CROSS-REFERENCE TO RELATED APPLICATIONS

This application is the National Stage of International Application No. PCT/EP2009/063684 International Filing Date 19 Oct. 2009, which designated the United States of America, and which International Application was published under PCT Article 21 (s) as WO Publication No. WO2011/047710 A1, the disclosures of which are incorporated by reference in their entireties.

BACKGROUND

1. Field

This patent application refers to a modular sample store for storing biological, chemical and/or biochemical samples. More particularly, this application refers to a temperature controlled modular sample store for storing such samples at controlled temperature conditions, in the range of +25° C. to −20° C. Most particularly, this application refers to a temperature controlled modular low temperature sample store for storing such samples at controlled temperature conditions, in the range of −25° C. to −90° C.

According to aspects of the disclosed embodiment, such a sample store includes:

(a) a storage area for taking up a number of storage stacks, which are accomplished for being inserted in an essentially vertical direction and for storing sample containers therein;

(b) a service area that is located adjacent to the storage area;

(c) a transfer area that is located above the storage area and the service area; (d) a motorized robot that is located in the transfer area and that is movable in at least one essentially horizontal direction; and (e) a controller (10) for controlling all actions and movements of the motorized robot (7).

Typically, the robot comprises a lifting device for lifting storage stacks at least partially out of the storage area and into the transfer area and for lowering storage stacks into the storage area and at least one platform for transporting at least one sample container within the transfer area.

2. Brief Description of Related Developments

Biological samples, such as body fluids (e.g. blood, urine, sputum or sperm), cells (e.g. bacterial cell cultures), or tissue samples (e.g. taken from human, animals or plants) are extremely temperature sensitive and have to be cooled or frozen immediately after taking the samples in order to prevent their destruction. Thus, an important aspect during investigation of biological samples and temperature sensitive samples in general is storage and provision of these samples in frozen state, i.e. at low temperatures. Storage and provision can be done in commercially available freezers (i.e. at temperatures of at most −18° C.), in a gas atmosphere that is cooled by dry ice (i.e. solid C02) to −78.5° C., or in liquid nitrogen (at −196° C.). In addition, freezers operating with compressors are known which provide storage temperatures of −35° C. (single-stage), −85° C. (double-stage), or −135° C. (triple-stage).

All these storage procedures and apparatuses are well known, but also provide certain drawbacks. Samples stored at a temperature of −18° C. can exhibit destruction artifacts already after short storage terms because of growing ice crystals. Such ice crystal growth is considerably reduced at dry ice temperatures and essentially does not take place in liquid nitrogen. However on the one hand, dry ice cooled containers warm up relatively fast as soon as all of the C02 has sublimated. On the other hand, storage in liquid nitrogen is cumbersome and only possible with dedicated safety measures and appropriately educated personal. Especially for robotic or automated storage and withdrawal/provision of a large number of samples there exist only very few of the known systems. Chemical samples (e.g. prepared reagent aliquots of defined concentration) and biochemical samples (e.g. concentrated and purified enzymes) are known to be stored more and more in automatic storage systems for large laboratories with the task of being provided and accessible at any time. In so called "large stores" or "bio-banks", storage temperatures of about −20° C. for chemical samples and of about −80° C. for biological and biochemical samples have proven to be reasonable.

From the U.S. Pat. No. 6,357,983 B1, an automatic storage system is known. In a conditioned chamber, the temperature of which being selectable in a range from −20° C. to +20° C., there are located two ring-like, nested shelves, which are rotatable around a common central axis, and which comprise a large number of horizontally orientated, superimposed shelf board positions. These shelf board positions can be accessed by a robot that moves vertically and outside of the shelves. This robot is equipped with an especially articulated gripper mechanism in order to reach to an inner shelf board position by penetrating an adjacent outer shelf board position. This system has the advantage that the robot, and thereby the sample, are located within the cold atmosphere during the entire process of selecting the sample, and that the sample can be moved out of the store via a lock. However, this system seems to be rather limited in the number of shelf boards, which results in cooling down a relatively large volume that can take up only a quite small number of samples. Moreover, a rather complex robot mechanism has to be utilized.

Another storage system for storing and providing frozen samples is known from the patent application EP 1 939 561 A2. This document discloses a compact storage system and a related method for storing frozen samples in such a compact storage system, which comprises a storage area within a thermally insulated housing that is equipped with a cooling device for cooling the storage area to at least −15° C. This compact storage system comprises revolving storage shelves in the form of a paternoster that are arranged entirely within the cooled storage area. This compact storage system also comprises a transfer area that is located above said storage area, a robot being moveable in essentially horizontal directions within this transfer area. The robot is accomplished to load a storage shelf into or to remove a storage shelf from the uppermost position of the upper half circle of the revolving storage shelves. The robot can also take out from a storage shelf or insert a single object into a storage shelf that is located at this vertex position of the paternoster. The storage area of this system appears to be quite compact. However, the mechanics of the paternoster have to be moved at temperatures down to −80° C.; because of the danger of frost condensation and thereby blocking the mechanics of the paternoster, elaborate and expensive measures are believed to be essential.

Other storage systems of the company REMP AG (Oberdiessbach, Switzerland) are known, in which samples are stored at +4° C. or −20° C. (REMP Small-Size Store™), or in which samples are stored at −80° C. (REMP Bio-Sample Store™). In the latter, a robot is implemented that is fully operable at −20° C.

Again another storage system is known from the U.S. Pat. No. 6,694,767 B2. Below a working area with controlled atmosphere, in which a robot with workplace is arranged, is located a thermally completely insulated storage space that is accomplished for storage temperatures of −85° C. to −80° C. Storage shelves with relatively small horizontal dimensions and numerous shelf boards superimposed to each other are vertically suspended in openings of the thermally insulating ceiling of the storage area. The storage shelves comprise an upper cover, that carries the storage shelf and that closes the opening in the thermally insulating ceiling in which the storage shelve is completely inserted. A robot lifts such a storage shelf out of the storage area in order to allow accessing a particular shelf board by an appropriate tool for removing a sample container from that shelf board of for depositing a sample container on that shelf board. Although the C02 atmosphere of the working area is dehumidified in order to reduce condensation of H20 on the cold surfaces of the sample containers during withdrawal of a shelf from the cooled storage area, there is the danger of warming up or even thawing the sample in the sample container. In addition, the time requested for depositing a sample container in the sample store or for taking out a sample container from this sample store is deemed to be too long; especially when large numbers of samples have to be provided within a short time.

BRIEF DESCRIPTION OF THE DRAWINGS

The sample store according to aspects of the disclosed embodiment is now described in detail with the help of drawings that point to one preferred exemplary embodiment without limiting the scope of the disclosed embodiment.

DETAILED DESCRIPTION

Figure 1:
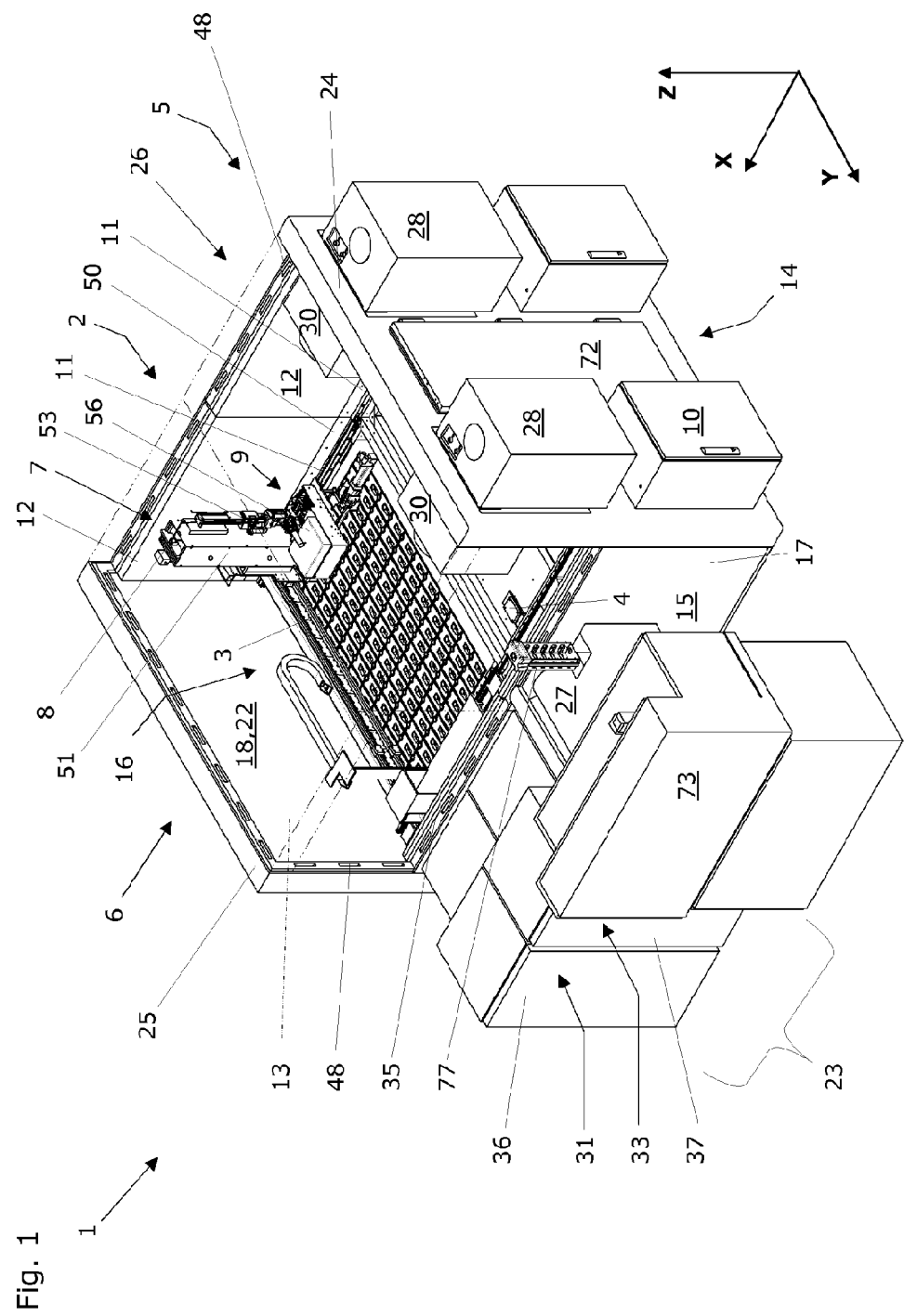
FIG. 1 shows a 3D graph of the smallest working embodiment of a low temperature sample store according to the disclosed embodiment.

FIG. 1 shows a 3D graph of the smallest working embodiment of a low temperature sample store according to the disclosed embodiment. This is, in general, a sample store 1 that comprises a storage area 2 for taking up a number of storage stacks 3, which are accomplished for being inserted in an essentially vertical direction and for storing sample containers 4 therein. This sample store further comprises a service area 5 that is located adjacent to the storage area 2 and a transfer area 6 that is located above the storage area 2 and the service area 5. In addition, the sample store comprises a motorized robot or transport assembly 7 that is located in the transfer area 6 and that is movable in at least one essentially horizontal direction. However, in another aspect the robot 7 is movable horizontally in an X-direction and in a Y-direction as indicated on the right side of the FIG. 1. The robot 7 comprises a lifting device or stack picker 8 for lifting storage stacks 3 at least partially out of the storage area 2 in an essentially vertical or Z-direction and thus, into the transfer area 6. The lifting device 8 of the robot 7 also serves for lowering storage stacks 3 into the storage area 2. The robot further comprises at least one platform 9 for transporting at least one sample container 4 within the transfer area 6.

In the context with the disclosed embodiment, the term "sample container" is to be understood as a standard multi-well microplate according to the ANSI/SBS standards 1-2004 and 2-2004 or a multi-well microplate with comparable dimensions. The term "sample container" is also to be understood as a rack for inserting micro-tubes as e.g. published in EP 0 904 841 B1; such racks may have similar or identical dimensions as standard microplates. Further, the term "sample container" is to be understood as a cell culture flask that has similar dimensions as a standard microplate and that can be stored in an essentially horizontal position. A blood bag is another "sample container" in the context with aspects of the disclosed embodiment; such blood bags could be supported by a tray that has about the same footprint like a standard microplate.

This sample store 1 also comprises a controller 10 for controlling all actions and movements of the motorized robot 7. This controller may be a central computer that is incorporated into the sample store 1; the controller may also be an external processor, to which the sample store operatively is connected.

The service area 5 of the sample store 1 comprises one integrally formed cubic vat module 11 and the storage area 2 of the sample store 1 comprises at least one integrally formed cubic vat module 11. Each one of said vat modules 11 comprises an essentially horizontal vat floor 14 and four joining vat walls 15 that are connected to the vat floor 14 and that are leaving an open vat space 16. Each vat floor 14 and vat wall 15 comprises an outside liner 17 and an inside liner 18, which outside and inside liners 17,18 in each case are separated by a clearance 19 that essentially is filled with a polymer foam material 20. This polymer foam material 20 provides fixation of the outside and inside liners 17,18 to each other as well as thermal insulation of and reinforcement to the thus integrally formed cubic vat module 11 sandwich construction.

There are different feasible embodiments of such sandwich constructions for forming an integrally formed cubic vat module 11.

In one aspect, said outside liner 17 may be a, powder coated, steel sheet, wherein said polymer foam material 20 is poly-urethane foam, and wherein said inside liner 18 is a multiplex plate 21 covered with a stainless steel sheet 22. Utilization of a stainless steel 22 sheet for the innermost surface of such an integrally formed cubic vat module 11 is preferred, because it provides absolutely pore-free surfaces and support perfect cleaning.

In another aspect, other sandwich-elements are combined to an integrally formed cubic vat module 11. Here, the outside liner 17 may be a powder coated, hard plastic sheet, the polymer foam material 20 again is polyurethane foam, and the inside liner 18 is a stable stainless steel sheet 22.

In the context of the aspects of the disclosed embodiment, the term "multiplex plate" is to be understood as "veneer plywood", which is assembled from at least five middle layers (veneer layers) typically from beech, birch, spruce or maple, each middle layer having a thickness of 0.8 to 2.5 mm. The number of middle layers varies according to the desired total plywood thickness from 5 to 55 and even more. The visible outer layers of the multiplex plates also vary considerably; there are painted surfaces, veneers of other kind of wood, or metal claddings. Plates are compressed with adhesive or water resistant resins and mutually barred (i.e. cross bonded), the texture of the single middle layers being offset typically by about 90°.

The elements (vat floor 14 and vat walls 15) of such an integrally formed cubic vat module 11 are fixed to each other by welding the inside liners 18 to each other and by welding or gluing the outside liners 17 to each other. Prior or after these fixings, the intermediate spaces 19 are filled with polymer foam material 20. Alternatively, these elements are fixed to each other by a dovetailed (preferably covered) connection like it is known from connections of wooden parts or sandwich plates; in such cases welding preferably is carried out after connecting the elements, e.g. by partial gluing of the polymer foam material 20 from adjacent elements.

As shown in FIG. 1 (see also FIG. 2), the sample store 1 also comprises upper side walls 12 and cover plates 13 to close the sample store at its top. The upper side wall plates 12, cover plates 13, front wall plate 24 and a back wall plate 25 may be of a simpler sandwich construction than the vat floor 14 and vat walls 15. The outside liner 17 may be a powder coated, hard plastic sheet, the polymer foam material 20 may be polyurethane foam, and the inside liner 18 is a stainless steel sheet 22. Alternatively, the upper side wall plates 12, cover plates 13, front wall plate 24 and a back wall plate 25 are of the same sandwich construction like the floor 14 and wall 15 of the integrally formed cubic vat module 11.

In one aspect the integrally formed cubic vat module(s) 11 of the storage area 2 and the service area 5 have the same size. This provides the advantage of larger number and thus, more economic production of integrally formed cubic vat modules. In another aspect each integrally formed cubic vat module 11 is equipped with two upper side wall plates 12 and one cover plate 13 that have the same length as one of the vat modules 11. In consequence, a functional segment 23 of the sample store 1 is formed by the elements: one integrally formed cubic vat module 11; two upper side wall plates 12; and one cover plate 13. A sample store 1 may also comprise a front wall plate 24 and a back wall plate 25 to close the sample store 1.

The smallest sample store 1 therefore (see FIG. 1) includes:
  two integrally formed cubic vat modules 11;
  four upper side wall plates 12;
  two cover plates 13;
  a front wall plate 24; and
  a back wall plate 25.

Adding a second functional element (with one integrally formed cubic vat module 11; two upper side wall plates 12; and one cover plate 13) will double the storage capacity of a sample store (1). Adding a third such functional element will triple the storage capacity of a sample store (1). It is thus clear to every skilled person that adding or removing a functional segment 23 or module will not alter the functionality of the previously present functional segments 23 or modules of a sample store 1. In order to fully support such scalability (for up-scaling as well as for down-scaling) and for always enabling the robot 7 moving over practically the entire transfer area 6 of a sample store 1 (before and after adding or withdrawing a functional segment 23), each integrally formed cubic vat module 11 of the storage area 2 and of the service area 5 comprises leveled carrying structures 49 on the vat side walls 35 and vat longitudinal walls 41 (see FIGS. 2-5 and 7). These leveled carrying structures 49 support horizontal rails 50 (see also FIGS. 1-3 and 8) for moving the robot 7 in an X-direction. Preferably, these horizontal rails 50 of each functional segment 23 are of such construction that they inter-digitate with the adjoining horizontal rails 50 of the neighbor functional segments 23. Alternatively but not preferably, parts of or the entire horizontal rails can be replaced to complete up-scaling or down-scaling of a modular sample store 1.

The sample store 1 also comprises a number of storage stacks 3 that are inserted in an essentially vertical direction into the open vat space 16 of one of the vat modules 11 in the storage area 2 and that are accomplished for storing sample containers 4 in an essentially horizontal position therein.

All sample stores may comprise an interface unit 26 that is located in a part of the transfer area 6, which is situated over the service area 5. The interface unit 26 comprises the service area 5 and a lock 27. The lock 27 is accomplished for locking-in sample containers 4 into the sample store 1 and for locking-out sample containers 4 out of the sample store 1. The lock 27 is accomplished as a drawer that is movable across the vat wall 15 where the lock is situated. This drawer can be hand driven or motor driven; proper closing of the lock 27 is monitored by the controller 10. In one aspect the robot 7 of the sample store 1 is implemented for transporting at least one sample container 4 to and from the interface unit 26. Such a simple sample store according to a first embodiment can be placed in a climatized or air-conditioned room, so that the sample store 1 itself does not need to be equipped with own means for conditioning the air inside.

The sample store 1 in one aspect is accomplished as a temperature controlled sample store and comprises at least one temperature control device 28. This temperature control device 28 is accomplished for circulating the air in the service area 5 and in the transfer area 6 of the sample store 1 and for controlling the air temperature to at most +25° C. Depending on the capacity of the temperature control device 28, lower temperatures such as at most +4° C., and in another aspect at most −20° C. can be controlled in-side a temperature controlled sample store. It is preferred to locate said at least one temperature control device 28 (or two temperature control devices 28 if necessary) in working connection with the interface unit 26. It is especially preferred to locate the temperature control devices 28 in connection with openings in the front wall plate, where also a door 72 is located (see FIG. 1). Such a door 72 can be used for service activities, when service work inside of the sample store is necessary.

A user interface (such as a touch screen), which is operatively connected to the controller 10, is provided close to the position of the lock 27 (not shown).

Figure 3:
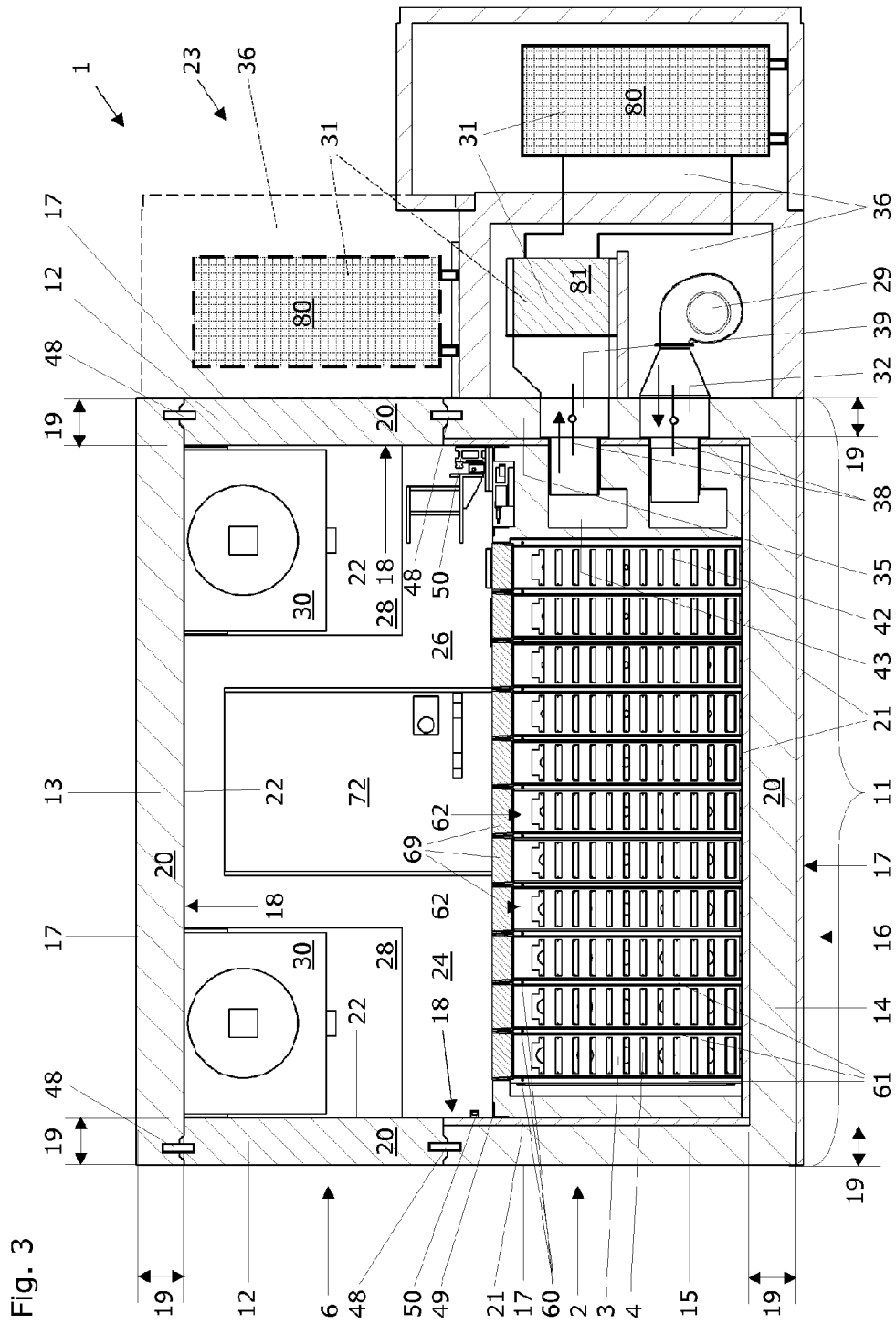
FIG. 3 shows a vertical cross-section in a Y-direction through the storage area and the transfer area of the low temperature sample store of FIG. 1.

It is clear from the FIG. 1 that the interface unit 26 is providing the sample store with all facilities for moving samples into and out of the sample store (see e.g. lock 27), for controlling all facilities of the sample store (see controller 10), for controlling the air temperature in the range from −20° C. to at most +25° C. (see temperature control devices 28), and for entering the ample store (see door 72). However, each integrally formed cubic vat module 11 of the storage area 2 of the sample store may include a first air outlet opening 32 and a first air inlet opening 39 (cv. FIG. 3) located in a vat side wall 35. To the first air outlet opening 32 is connected a ventilator 29 for circulating the temperature controlled air in the integrally formed cubic vat module 11 of the storage area 2.

A workstation 73 with liquid handling capability (such as e.g. a Freedom EVO® Assay Workstation of Tecan Trading, CH-8708 Mannedorf, Switzerland) can be installed adjacent to a modular sample store 1 to exchange sample containers 4 with the sample store 1 (see FIG. 1) using the lock 27 of the sample store 1. Alternatively, such a workstation 73 can be connected to the sample store by a conveyor belt 79 that leads to a single plate interface 78, which is located in the interface unit 26 (see FIG. 4). In this case again, the lock 27 is used to open and close the way into and out of the modular sample store 1. The motorized robot 7 is able to remove a locked-in sample container 4 from the single plate interface 78 by the help of a Z-module or sample container lifting module 53 (see FIG. 8A). This Z-module 53 is accomplished for lifting a sample container 4, e.g. in the form of a microplate-sized micro-tube rack (see FIG. 8B) in a vertical Z-direction and for setting said sample container 4 onto a first carrier 54 or onto a second carrier 55 of the robot 7. After picking-up the sample container 4 from the single plate interface 78, the robot will deposit the sample container 4 in an in/out stack 77, in a pre-in/out stack or in a storage stack 3.

In such a temperature controlled sample store 1, the storage stacks 3 are not equipped with individual insulating covers 69 as shown in the FIGS. 1-4 and 6-8, because it is essential that the temperature controlled air can freely circulate in the entire inside of such a temperature controlled sample store 1.

The sample store 1 in another aspect is accomplished as a temperature controlled low temperature sample store and comprises at least one cooling device 30 for cooling and controlling the air temperature to at most −20° C. This cooling device 30 is accomplished for cooling and controlling the air temperature to at most −20° C. and for circulating the cooled air in the service area 5 and in the transfer area 6 of the sample store 1. This at least one cooling device 30 is located in working connection with an interface unit 26. It is preferred to locate said at least one cooling device 30 (or two cooling devices 30 if necessary) in working connection with the interface unit 26. It is especially preferred to locate the cooling devices 30 in connection with openings in the front wall plate, where also a door 72 is located (see FIG. 1).

The temperature controlled low temperature sample store 1 also comprises temperature control devices 28 that are combined with the cooling devices 30. It is especially preferred to install two temperature controlling units, each of which is accomplished as a combination of a temperature control device 28 and a cooling device 30. Installation of two such temperature controlling units provides redundancy of the temperature regulating instruments such that in case of failure of one of these temperature controlling units, the other temperature controlling unit will take over responsibility of temperature control.

It is clear from the FIG. 1 that the interface unit 24 is providing the sample store with all facilities for moving samples into and out of the sample store (see e.g. lock 27), for controlling all facilities of the sample store (see controller 10), for cooling and controlling the air temperature in the range of −20° C. (see temperature control devices 28 and cooling devices 30), and for entering the sample store (see door 72). In addition, each integrally formed cubic vat module 11 of the storage area 2 of the temperature controlled low temperature sample store comprises at least one deep cooling device 31 for deep cooling the air to a temperature of at least −80° C. and at least one ventilator 29 that are connected to one first air outlet opening 32 and to one first air inlet opening 39 located in a vat side wall 35 for circulating the deep cooled air in the integrally formed cubic vat module 11 of the storage area 2 of the sample store 1.

In such a temperature controlled low temperature sample store 1, the storage stacks 3 always are equipped with individual insulating covers 69 as shown in the FIGS. 1-4 and 6-8, because it is essential that deep cooled air in the integrally formed cubic vat module 11 of the storage area 2 of the sample store 1 cannot escape the storage area 2 and cannot freely circulate in the entire inside of such a temperature controlled low temperature sample store 1.

In one aspect the at least one deep cooling device 31 and one ventilator 29 are accommodated in one single common housing 36 (not shown), which is located outside the vat module 11. The single common housing 36 can be located in some distance to the temperature controlled low temperature sample store 1 (not shown) and it can be in working connection with each one of the vat modules 11 via cooling lines (not shown) that are connected to said first air outlet and inlet openings 32,39 located in each one of the vat side walls 35 of the vat module 11 to be cooled to low temperatures.

In another aspect each one of the integrally formed cubic vat modules 11 of the storage area 2 of the sample store 1 comprises at least one individual first deep cooling device 31 and at least one individual ventilator 29 that are accommodated in one common housing 36 (see FIG. 3). This common housing 36 is located at the vat side wall 35 outside the vat module 11. This common housing 36 is in direct working connection with the respective vat module 11 via said first air outlet and inlet openings 32,39. Of special preference is that each integrally formed cubic vat module 11 of the storage area 2, according to this second variant, comprises second air outlet and inlet openings 34,40 situated in the vat side wall 35 (see FIGS. 5 and 7), to which second air outlet and inlet openings 34,40 is connected an individual second deep cooling device 33, which is located in a separate housing 37 at the vat side wall 35 outside the vat modules 11 (see FIGS. 1 and 4). In one aspect, a deep cooling device 31,33 comprises a deep cooling aggregate 80 and an evaporator 81 (see FIG. 3). Alternatively, the positions of the ventilator 29 and the evaporator 81 of an individual deep cooling device 31,33 can be switched, so that the ventilator 29 is located on top of the evaporator 81 (not shown).

Selection of the cooling capacity of the individual first and second deep cooling devices 31,33 may be such that in the everyday duty, the first and second deep cooling devices 31,33 are only working with at least 50% of their cooling capacity. In the case of failure of one of these deep cooling devices 31,33 (both dedicated to a single vat module 11), the still working device can take over at least a considerable part of the cooling capacity of the defective device. Taking over such responsibility can result in about 80% of the every day cooling capacity, enabling a more limited handling of the sample containers 4 stored in the respective storage stacks 3. However, providing full cooling capacity by the still working deep cooling device 31 or 33 is preferred. In consequence, full deep cooling capacity is guaranteed also in the case of failure of one of these deep cooling devices 31,33. As a result, full sample integrity is guaranteed.

In an alternative arrangement, but not departing from the spirit of the preset invention, one part for the common housing 36 can be located on top of the other (see FIG. 3, dashed lines). Thus, the aggregate 80 will be located on top of the evaporator 81.

The temperature controlled low temperature sample store 1 of the aspects of the disclosed embodiment may be equipped with air stopping means that allow functional separation of individual deep cooling components from the vat space 16 or vat spaces 16. This is achieved in that each one of said first and second air outlet openings 32,34 and each one of said first and second air inlet openings 39,40 is equipped with a shutter 38. These shutters 38 are accomplished for closing the respective openings 32,34,39,40 and thus separating one of a ventilator 29, a combination of a first deep cooling device 31 and a ventilator 29, and a combination of a second deep cooling device 33 and a ventilator 29 from the integrally formed cubic vat module 11 of the storage area 2 of the sample store 1 to which said openings 32,34,39,40 guide. These shutters 38 may be motor driven and controlled in their position by the controller 10. As the controller 10 may also receive information about the status of the aggregate 80 and of the evaporator 81, individual automatic deicing of the first and second deep cooling devices 31,33 is possible. During such a deicing procedure, the other deep cooling device is in operation in order to provide sample integrity, i.e. in order to prevent the samples in the sample containers 4 from being heated to too high temperatures.

Because of equipping each storage vat module 11 with shutters 38, functionally disconnecting accessories, like ventilators and deep cooling devices from the storage vat modules allows full servicing of these accessories without being obliged to thaw and empty a storage vat module. Also thawing of a single storage vat module can be carried out while all other storage vat modules are kept in operation and at temperatures down to −90° C.

Figure 5A:
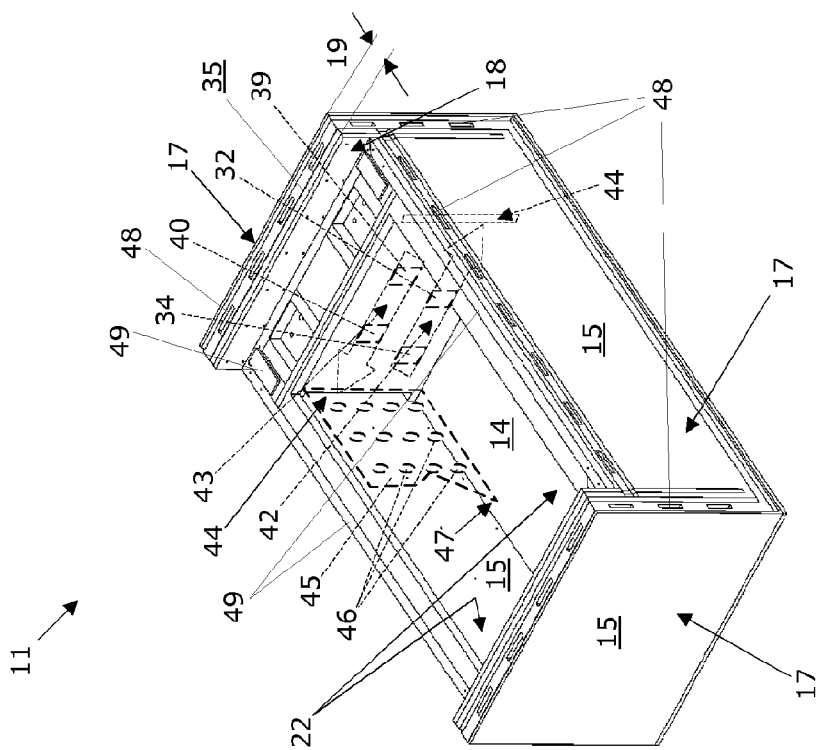
FIG. 5A shows the vat side wall of an integrally formed cubic vat module with the air inlet and air outlet openings from the outside.
Figure 5B:
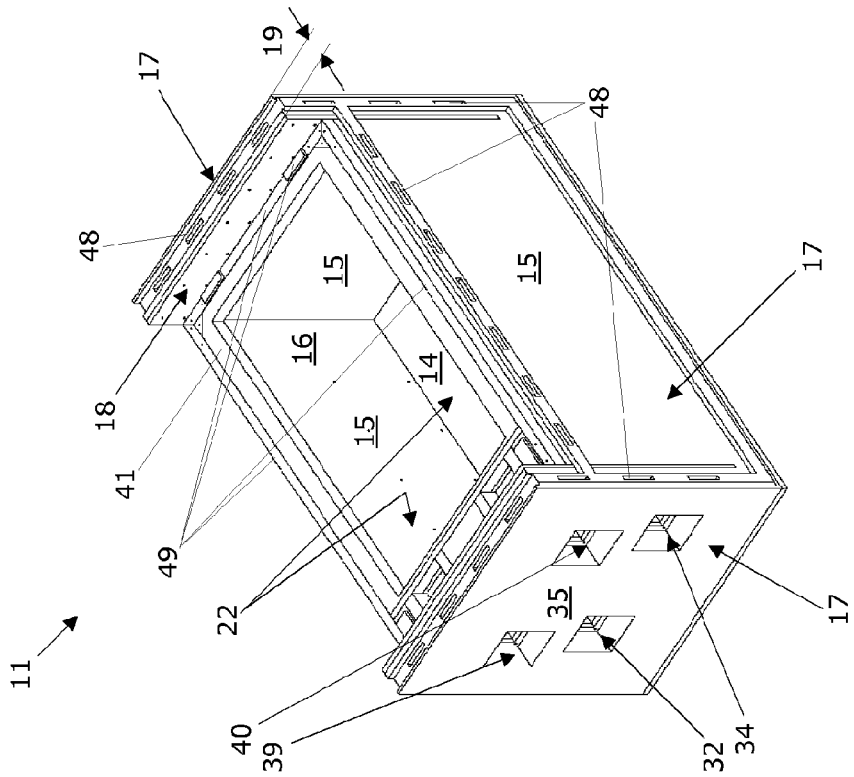
FIG. 5B shows the vat side wall of the cubic vat module of FIG. 5A with the air inlet and air outlet openings from the inside.

To achieve more homogeneous distribution of deep cooled air inside the storage vat modules 11, each vat module 11 of the storage area 2 also comprises an air out channel 42 and an air in channel 43 (see FIG. 5A). These two channels 42,43 are situated at the inside of the vat side wall 35 (see FIG. 7) and these two channels 42,43 mouth to inner openings 44. The inner openings 44 lead to the vat space 16 of each vat module 11 of the storage area 2. The air out channel 42 is connected to the air outlet openings 32,34 and the air in channel 43 is connected to the air inlet openings 39,40 (see FIGS. 3 and 5). Each one of said inner openings 44 is located close to a longitudinal vat wall 41 that join said vat side wall 35 (see FIG. 5B), and two air guiding blades 45 with ventilation holes 46 are positioned in a distance 47 to one or the other of the longitudinal vat walls 41 for distributing deep cooled air to or collecting deep cooled air form the vat space 16 (see FIG. 5B).

Each construction part selected from the group comprising the integrally formed cubic vat modules 11, the upper side walls 12, and the cover plates 13 has mechanical connecting elements 48 for reversibly connecting two of these construction parts mutually. Such mechanical connecting elements advantageously are accomplished as a hook-like tension catch in the one construction part and a respective locking plate in the other construction part. On the one hand, closely connecting two construction parts is achieved, and on the other hand relatively simple separation is possible later. Special tools to move the hook-like tension catches in order to exert higher forces may be used. Embedding these tension catches and locking plates in the polymer foam material allows exertion of such forces without releasing these tension catches and locking plates from their seats. As can be seen from the FIGS. 1 to 5, 7 and 8, on all connecting surfaces between the construction parts of a sample store 1, a temperature controlled sample store 1, or a temperature controlled low temperature sample store 1, there are at least one, or more than one, or a series of mechanical connecting elements 48 present for mutually connecting these construction parts in reversible manner.

As mentioned earlier, for enabling the robot 7 moving over practically the entire transfer area 6 of a sample store 1, each integrally formed cubic vat module 11 of the storage area 2 and of the service area 5 comprises carrying structures 49 on the vat side walls 35 and vat longitudinal walls 41 (see FIGS. 2-5 and 7). These carrying structures 49 support horizontal rails 50 (see also FIGS. 1-3 and 8) for moving the robot 7 in an X-direction.

Figure 8A:
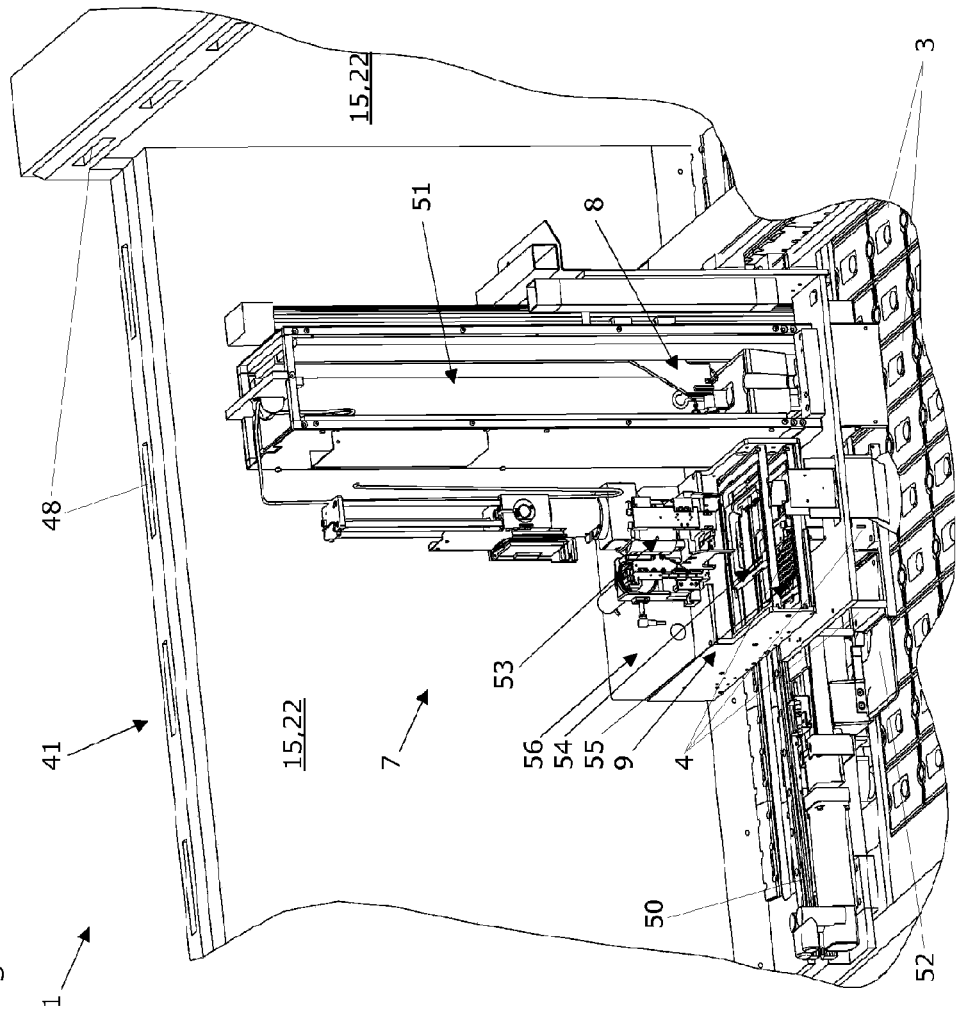
FIG. 8A shows the robot inside the transfer area of the low temperature sample store of FIG. 1.

The motorized robot 7 comprises an insulated hood 51 that is located in the transfer area 6 (see FIG. 8A). The robot 7, when using the lifting device 8 is capable to partially lift a storage stack 3 into said insulated hood 51. Actually, FIG. 8A shows lifting of a stack 3 at an early stage, the stack 3 being still almost entirely inserted in the vat space 16. The stack 3 then will be lifted up to a level, which is accessible by a spatula or picker 52 of the robot 7 (see FIG. 8A). This spatula 52 is accomplished to be moved into the insulated hood 51 and below a certain sample container 4. When the spatula is inserted into the insulated hood 51, it is preferred that the lifting device 8 incrementally lowers the stack 3 (e.g. by a few mm), thus enabling the selected sample container 4 to lay on the spatula 52 without contacting mutual storage webs 68 (see FIG. 6B) that previously carried the sample container 4. The robot 7 is accomplished to move said certain sample container 4 out of the storage stack 3 in horizontal direction. The robot 7 is further accomplished to move this or another sample container 4 into the storage stack 3 in horizontal direction.

Figure 4:
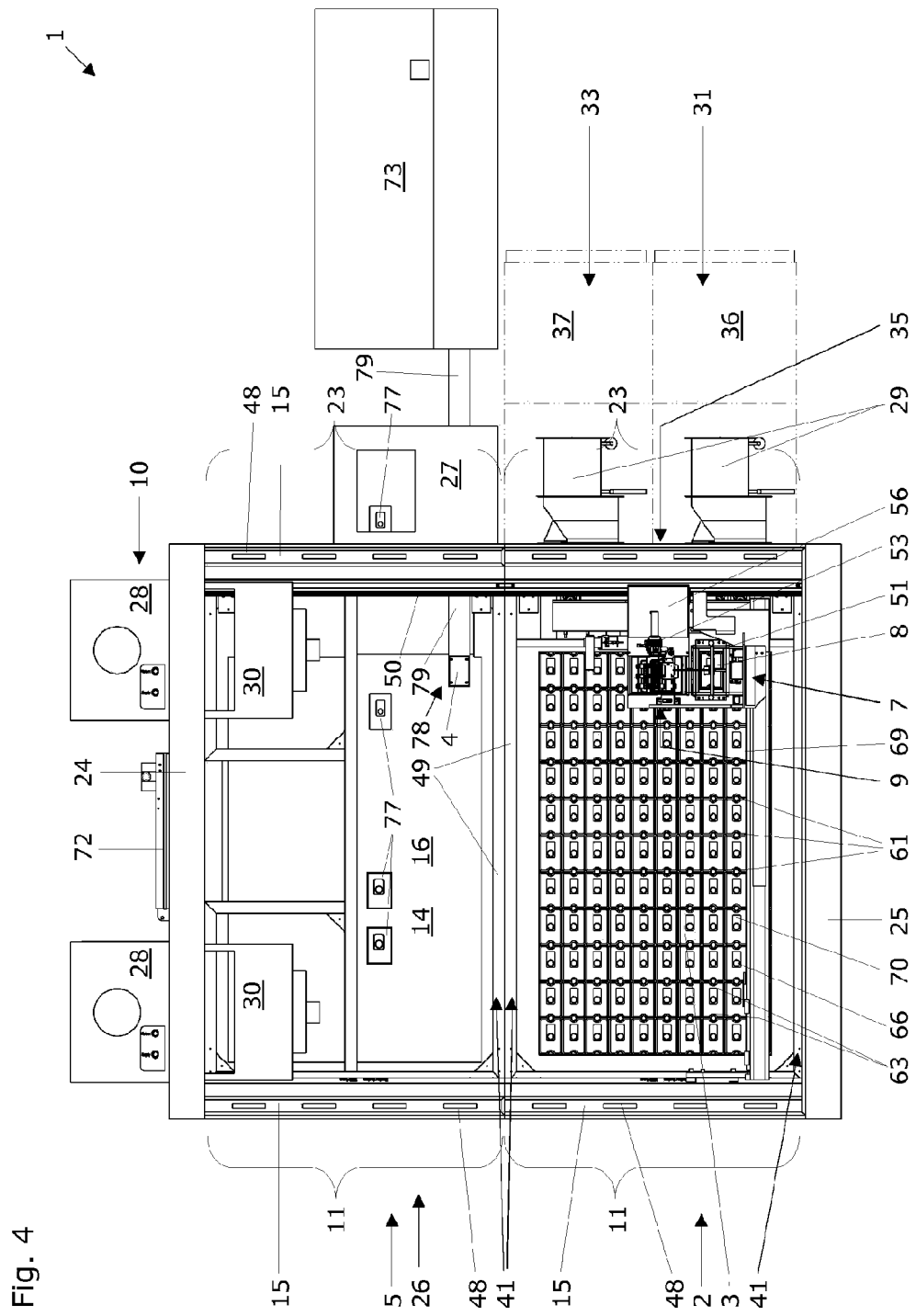
FIG. 4 shows a horizontal projection of the storage area, the service area, and the transfer area of the low temperature sample store of FIG. 1.

In/out stacks 77 can permanently be located in the interface unit 26 as well (see FIG. 4). In such case, the motorized robot 7 will only lift and lower these in/out stacks the same way as he does with the storage stacks 3 in the storage area 2. These in/out stacks therefore can be used as intermediate storage places for adapting sample containers 4 to the temperature of the interface unit (which may be −20° C.). This temperature adaption can be advantageous when loading sample containers 4 into the sample store 1 as well when taking sample containers 4 out of the sample store 1.

The motorized robot 7 comprises an insulated hood 51 that is located in the transfer area 6 (see FIG. 8A). The robot 7, when using the lifting device 8 is capable to partially lift a storage stack 3 into said insulated hood 51. Actually, FIG. 8A shows lifting of a stack 3 at an early stage, the stack 3 being still almost entirely inserted in the vat space 16. The stack 3 then will be lifted up to a level, which is accessible by a spatula 52 of the robot 7 (see FIG. 8A). This spatula 52 is accomplished to be moved into the insulated hood 51 and below a certain sample container 4. When the spatula is inserted into the insulated hood 51, it is preferred that the lifting device 8 incrementally lowers the stack 3 (e.g. by a few mm), thus enabling the selected sample container 4 to lay on the spatula 52 without contacting mutual storage webs 68 (see FIG. 6B) that previously carried the sample container 4. The robot 7 is accomplished to move said certain sample container 4 out of the storage stack 3 in horizontal direction. The robot 7 is further accomplished to move this or another sample container 4 into the storage stack 3 in horizontal direction.

When cooling the entire modular sample store 1 only down to a temperature of about −20° C., the motorized robot 7 may be void of an insulated hood 51, because at temperatures between +25° C. and −20° C. there is practically no temperature difference between the storage area 2, the transfer area 5, and the interface unit 26. Thus, utilization of an insulated hood 51 is not necessary. In consequence when using the lifting device 8, the motorized robot 7 is capable of partially lifting a storage stack 3 up to a level, which is accessible by its spatula 52 (see FIG. 8A). The spatula 52 is accomplished to be moved into the lifted storage stack 3 and below a certain sample container 4. When the spatula is inserted into the storage stack 3, it is preferred that the lifting device 8 incrementally lowers the stack 3 (e.g. by a few mm), thus enabling the selected sample container 4 to lay on the spatula 52 without contacting mutual storage webs 68 (see FIG. 6B) that previously carried the sample container 4. The robot 7 is accomplished to move (by withdrawal of the spatula 52) said certain sample container 4 out of the storage stack 3 in a horizontal direction and to move this or another sample container 4 into the storage stack 3 in a horizontal direction.

Figure 2:
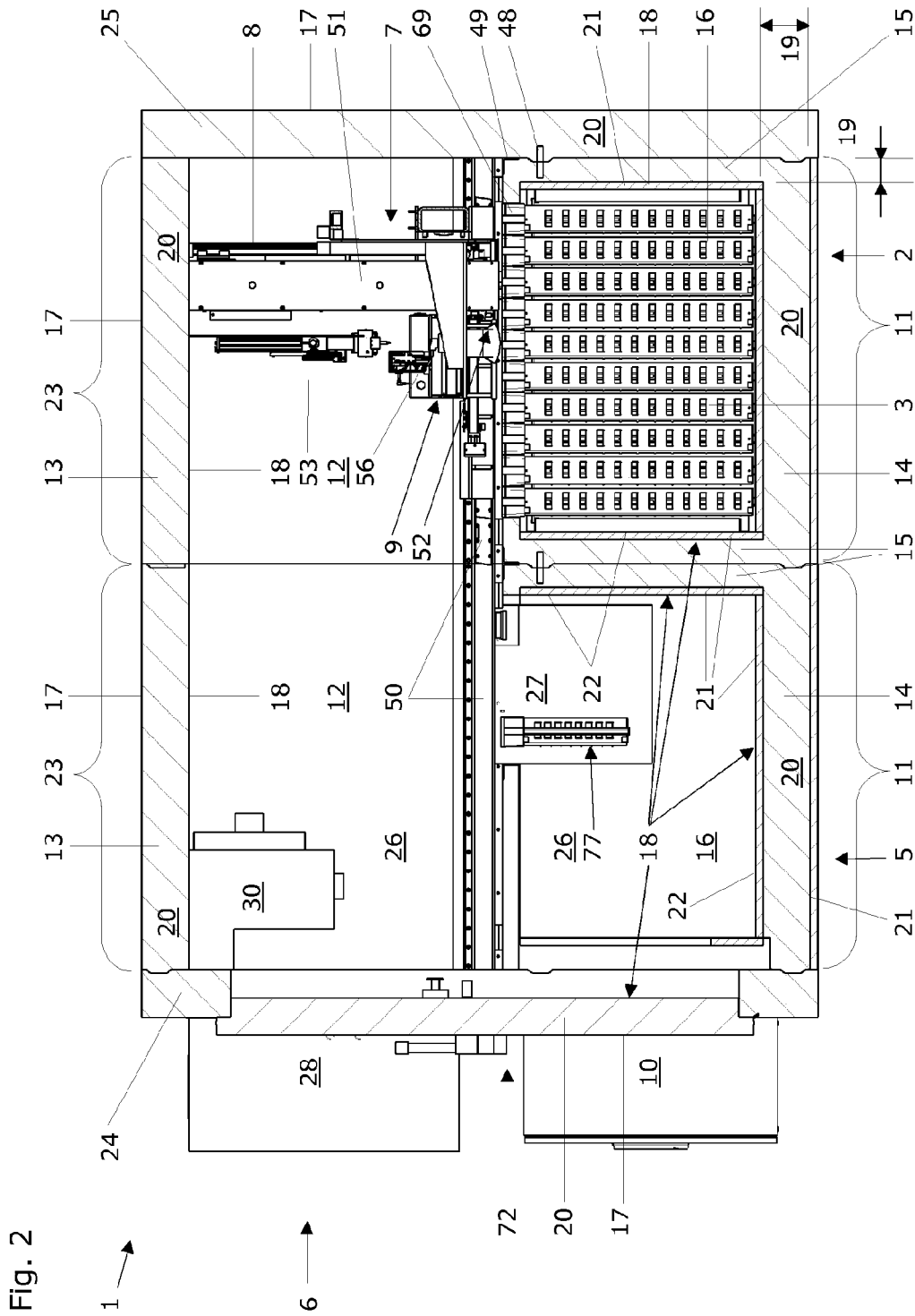
FIG. 2 shows a vertical cross-section in an X-direction through the storage area, the service area, and the transfer area of the low temperature sample store of FIG. 1.
Figure 8B:
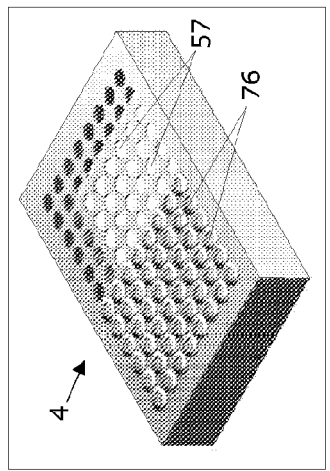
FIG. 8B shows a sample container in the form of a microplate sized rack for micro-tubes.

In order to be able to temporarily keep and transport one sample container 4, the robot 7 comprises the platform 9 (see FIGS. 1, 2, and 8). This platform 9 comprises two carriers 54,55. As mentioned earlier, the robot 7 further comprises a Z-module 53 (see FIG. 8A) for lifting a sample container 4, e.g. in the form of a microplate-sized micro-tube rack (see FIG. 8B), from the spatula 52 in a vertical Z-direction and for setting said sample container 4 onto the first carrier 54 or onto the second carrier 55. Both carriers 54,55 are individually moveable in a horizontal X-direction and in a horizontal Y-direction that is perpendicular to the X-direction.

Figure 8C:
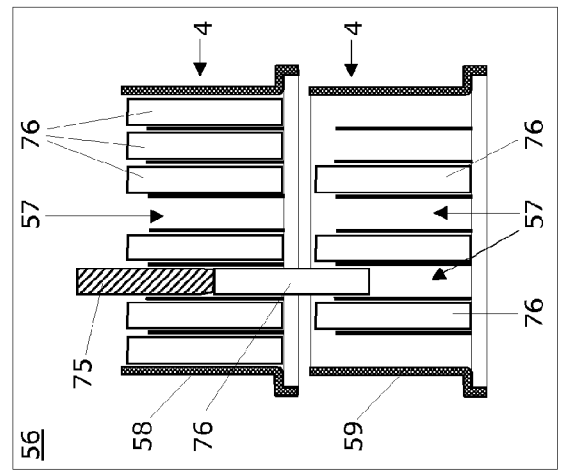
FIG. 8C shows two such racks of FIG. 8B superimposed as the source plate and the destination plate during punching of a micro-tube.

The robot 7 comprises a punching device 56 for pushing a micro-tube out of a compartment 57 of a first microplate-sized micro-tube rack or source plate 58 into a compartment of a second microplate-sized micro-tube rack or destination plate 59 (see FIG. 8C). For carrying out the so-called punching process, the source plate 58 may be located above the destination plate 59 and the punching device 56 is accomplished to pushing down a micro-tube in vertical Z-direction. Similar punching devices are known from e.g. EP 0 904 841 B1.

For safer storing the storage stacks 3 with the sample containers 4 in the vat space 16 of the storage area vat modules 11, each integrally formed cubic vat module 11 of the sample store storage area 2 comprises a guiding grid 60 (see FIG. 6A) that is located in the vat space 16. This guiding grid 60 is supported by guiding posts 61 (see FIGS. 6A and 6B) standing on the vat floor 14. This guiding grid 60 is defining an array of apertures 62 (see FIG. 6B) adapted to the size of storage stacks 3. Each one of the storage stacks 3 is accomplished to be vertically movable in one of these apertures 62. The guiding posts 61 partly engage slide grooves 63 (see FIG. 6B) located on two opposite vertical sides of the storage stacks 3 and guiding vertical movement of the storage stacks.

In one aspect, the storage stacks 3 comprise lateral support flanges 64 (see FIG. 6B) with carrying webs (not shown) that carry the weight of a storage stack 3 when it is lowered to its lowermost position in the vat space 16, the carrying webs of the lateral support flanges 64 being supported by the guiding grid 60.

Figure 6B:
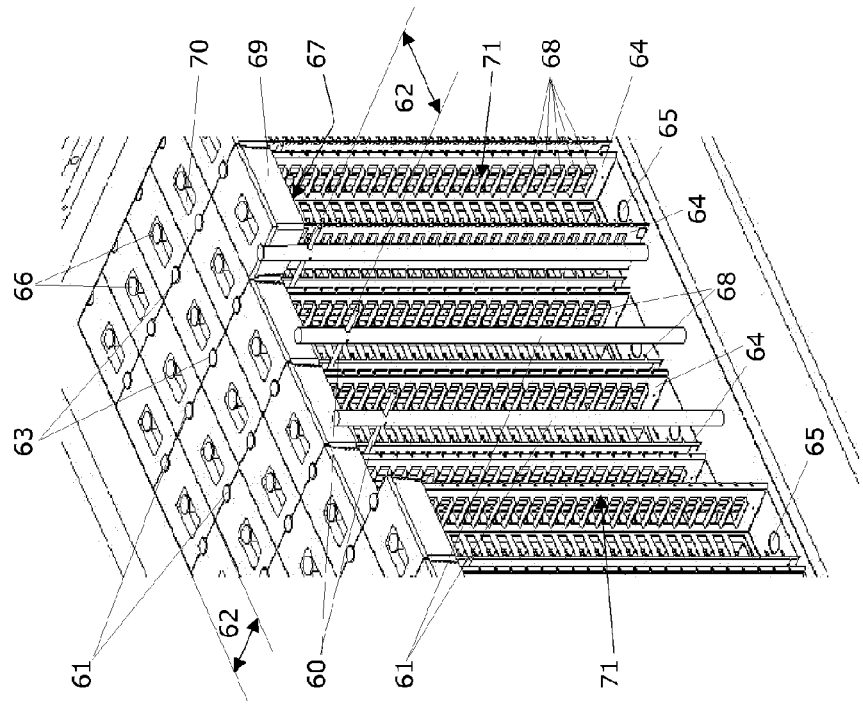
FIG. 6B shows the inside of a vat space of a storage vat module and an arrangement of a combination of the guiding grid and guiding posts with inserted storage stacks.
Figure 6A:
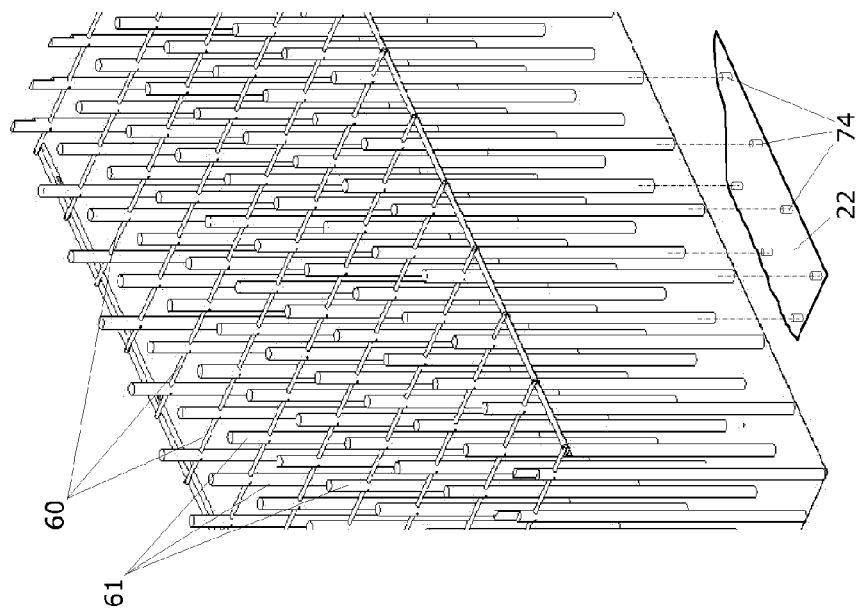
FIG. 6A shows the inside of a vat space of a storage vat module and an arrangement of a guiding grid attached to guiding posts.

In another aspect, the storage stacks 3 comprise an individual trunnion 65 at their lower end (see FIG. 6B). Said trunnion 65 carries the weight of a storage stack 3 when it is lowered to its lowermost position in the vat space 16 by abutting the vat floor 14.

Orientation pins 74 serve for orientating and positioning of the lower ends of the guiding posts 61. Such orientation pins 74 may be provided as welded bolts that are fixed onto the stainless steel sheet 22 of the vat floor 14 inside liner 18 (see FIG. 6A). Alternatively, the orientation pins 74 are provided as welded bolts that are fixed onto a separate stainless steel plate (with or without a number of additional holes in it) that is positioned on top of the stainless steel sheet 22 of the vat floor 14 inside liner 18 (not shown).

In order to be lifted by the lifting device 8 of the robot 7, each storage stack 3 comprises at its upper end a carrying element 66 (se FIG. 6B) that is engageable by the lifting device 8 and that is attached to a carrying structure 67 with lateral support flanges 64 that are equipped with mutual storage webs 68 for supporting one sample container 4 on top of the other and in a horizontal position (see FIG. 6B). At least a part of the carrying element 66 is made of a metal that can be detected by an orientation (not shown) sensor that works on an inductive or capacitive principle. With the help of such an orientation sensor, the motorized robot 7 is able to detect the actual position of the carrying element 66, which greatly facilitates controlling the necessary movements (down, horizontal, and up) of a carrying head of the lifting device (not shown) that is used to engage the carrying element 66 of a storage stack 3.

The motorized robot 7 is moving and acting in a three dimensional Cartesian coordinate system as indicated in FIG. 1. When e.g. loading sample containers 4 into the sample store or when retrieving sample containers 4 from the sample store 1, the controller 10 directs the robot 7 to the average position of a particular storage stack 4 or in/out stack 77. When arriving at this average position, a robot 7 that is equipped with such an orientation sensor can more easily and more exactly find the best position for engaging the carrying element 66 of the particular storage stack 3 as a result of a self-teaching operation. Later, the controller 10 notes these exact positions and it will then be able to instantly send the motorized robot 7 again to this more exact position thanks to the teaching of the robot 7.

Figure 7:
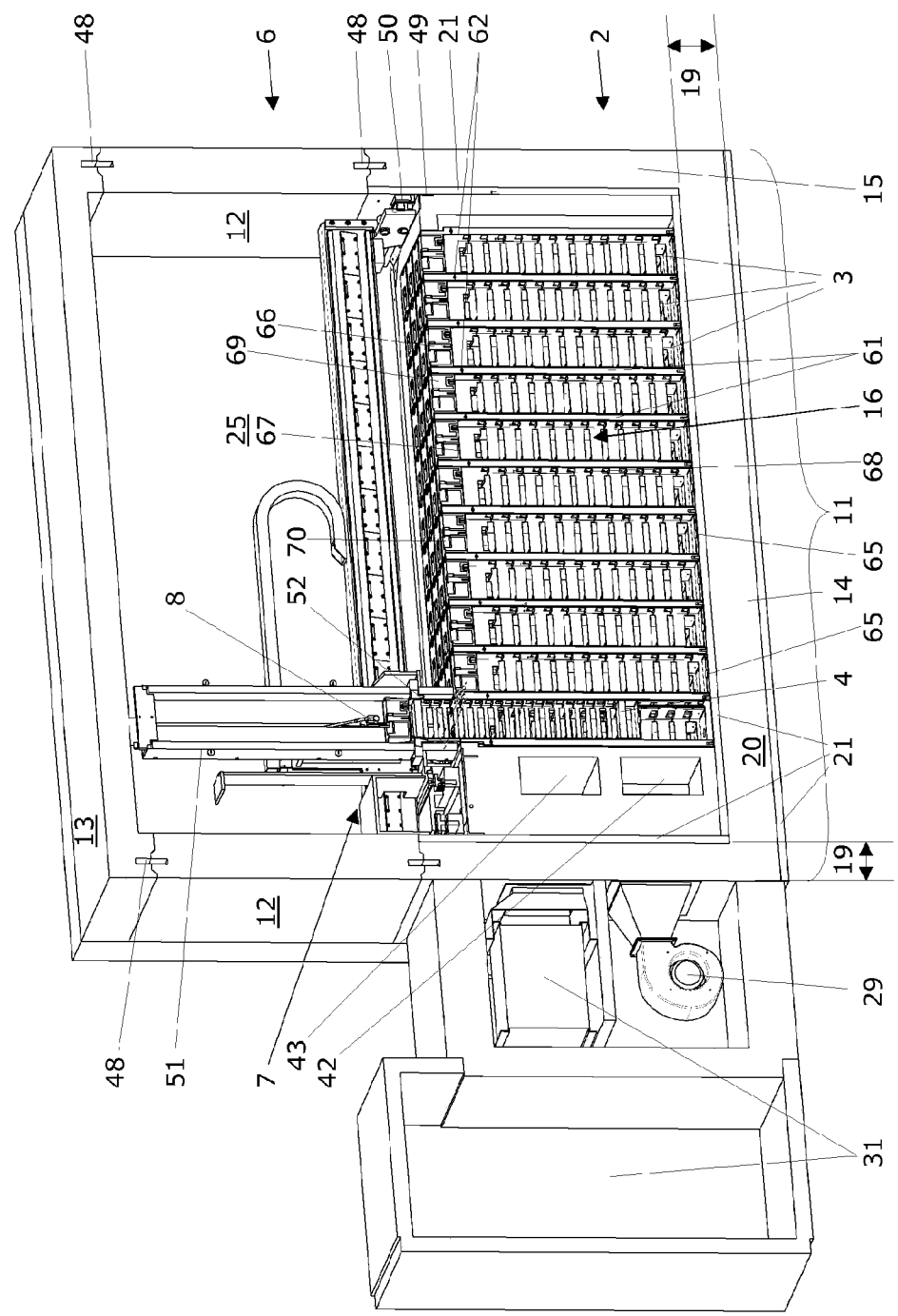
FIG. 7 shows a 3D cross section view in a Y-direction according to FIG. 3, but viewed in the opposite X-direction.

As described earlier, each storage stack 3 of a temperature controlled low temperature sample store 1 comprises an individual insulating cover 69 at its upper end (see also FIG. 7). The carrying element 66 of this storage stack 3 is located in a depression 70 on the upper side of the individual isolating cover 69 (see FIG. 6B).

It is known that storage at low temperatures may cause condensation of water vapor contained in the gas atmosphere. In order to minimize or to avoid such frost deposition, each storage stack 3 comprises surfaces to which is applied an anti-frost coating 71. Of special interest for the application of such anti-frost coatings are the surfaces of the mutual storage webs 68, which directly come into contact with the sample containers 4 to be stored. Other surfaces of special interest for the application of such anti-frost coatings are the surfaces of the guiding posts 61 and the sliding grooves 32 that interact with these guiding posts (see FIG. 6B). Coatings that can avoid or reduce frost deposition are known from e.g. EP 0 925 333 B1 and EP 0 352 180 B1, wherein anti-frost coatings from non-protein origin are preferred (see EP 0 352 180 B1).

The sample store 1, the temperature controlled sample store 1, and the temperature controlled low temperature sample store 1 according to the disclosed embodiment as well enable methods for storing and providing samples. One exemplary storage method for storing and providing samples in a sample store 1, includes:

(a) storing samples in a storage area 2 for taking up a number of storage stacks 3, which are accomplished for being inserted in an essentially vertical direction and for storing sample containers 4 therein;

(b) providing a service area 5 that is located adjacent to the storage area 2;

(c) providing a transfer area 6 that is located above the storage area 2 and the service area 5;

(d) providing a motorized robot 7 that is located in the transfer area 6 and that is movable in at least one essentially horizontal direction, the robot 7 comprising:

i) a lifting device 8 for lifting storage stacks 3 at least partially out of the storage area 2 and into the transfer area 6 and for lowering storage stacks 3 into the storage area 2; and ii) at least one platform 9 for transporting at least one sample container 4 within the transfer area 6; and (e) controlling all actions and movements of the motorized robot 7 with a controller 10.

The exemplary storage method for storing and providing samples is characterized in that the sample store 1 service area 5 is provided with one integrally formed cubic vat module 11 and the sample store 1 storage area 2 is provided with at least one integrally formed cubic vat module 11. Each one of said vat modules 11 comprise an essentially horizontal vat floor 14 and four joining vat walls 15 that are connected to the vat floor 14. Each one of said vat modules 11 leaves an open vat space 16. In addition, the sample store 1 is closed by also providing upper side walls 12 and a cover plate 13. Moreover, each vat floor 14 and vat wall 15 comprise an outside liner 17 and an inside liner 18. The outside and inside liners 17,18 in each case are separated by a clearance 19 that is essentially filled with a polymer foam material 20. This polymer foam material 20 provides fixation of the outside and inside liners 17,18 to each other as well as thermal insulation of and reinforcement to the thus integrally formed cubic vat module 11 sandwich construction.

Storing of a sample comprises the following steps:

(a) identifying and inserting a sample container 4 via a lock 27 into an interface unit 26 of the sample store 1;

(b) moving the sample container 4 with the robot 7 to a selected storage stack 3 with an empty storage position and positioning the sample container 4 on a spatula 52;

(c) lifting the selected storage stack 3 by the lifting device 8 of the robot 7 to a level that the empty storage position of the storage stack 3 is reachable by the sample container 4 positioned on the spatula 52;

(d) inserting into the empty storage position of the storage stack 3 the spatula 52 with the sample container 4 positioned thereon;

(e) lowering the storage stack 3 for an incremental distance to place the sample container 4 on lateral support flanges 64 of the storage stack 3;

(f) withdrawing the spatula 52 from the storage stack 3; and (g) lowering the storage stack to its lowermost position in the vat space 16 of the integrally formed cubic vat module 11 of the sample store storage area 2.

The spatula 52 comprises at least one parking position for placing a sample container 4. It is however especially preferred to equip the spatula with two parking positions for placing two sample containers 4 on the spatula (see FIG. 8A).

Identifying a sample container 4 comprises at least one of the following steps:

reading of a machine readable identifier of the sample container 4;

reading of additional information provided by the machine readable identifier; and measuring the average temperature of the sample container.

As known to skilled persons, machine readable identifiers comprise barcodes (ID, 2D, or 3D), RFID tags (Radio Frequency Identification tags), RuBee tags, and combinations of the same. The selected storage stack 3 with an empty storage position is chosen by the controller 10 according to at least one of:

the identifier of the sample container 4;

the additional information provided; and the average temperature of the sample container.

In order to read such machine readable identifiers, the sample store 1 is equipped with appropriate reading devices, such as barcode readers and RFID transponders. The reading devices are located next to the lock 27 and/or within the lock 27.

The selected storage stack 3 with an empty storage position is a pre-in/out storage stack or a permanent storage stack. Preferred identifiers comprise a name, a combination of alphabetic characters, a combination of numbers, a logo, and combinations thereof. The additional information may comprise information about the content of the sample container 4, information about an individual, the sample has been taken from, information about intended processing of the sample, information about processing to be avoided, information about maximum storage temperature, information about maximum storage time, and information about biohazard potential. Means for measuring the average temperature of the sample container comprise infrared temperature sensors.

The air in the storage, service, and transfer areas 2,5,6 of the sample store 1 may be kept at a temperature in the range from +25° C. to −20° C. for storing a sample. In one aspect the air in the storage area 2 may be kept at a temperature in the range from −20° C. to −90° C. and keeping the air in the service and transfer areas 5,6 may be kept at a temperature of −20° C. for storing biological samples.

In one aspect one storage method enables shortening of transfer distances inside the sample store 1 and comprises providing one or more pre-in/out stacks within the integrally formed cubic vat module 11 of the storage area 2, which is located adjacent to the integrally formed cubic vat module 11 of the service area 5. For this purpose, the interface unit 26 of the sample store 1 that comprises the lock 27 is located in that part of the transfer area 6 of the sample store 1 that is located above and that comprises the service area 5. Another storage method comprises keeping the temperature of the cooled air within the vat space 16 of the integrally formed cubic vat module 11 that contains the pre-in/out stacks at a temperature lower than −80° C., and in one aspect at −90° C., for compensating heat input by sample containers 4 arriving from the lock 27.

In one aspect a storage method, in which the motorized robot 7 that is controlled by the controller 10 inserts sample containers 4 into storage stacks 3 or withdraws sample containers 4 from storage stacks 3 according to a certain job request may be provided. The controller 10 forces the motorized robot 7 to interrupt a requested job, if the longest allowable presence of one of the sample containers 4 or micro-tube in that sample container 4 has reached a limit that has been set according to additional information, which has been provided by the machine readable identifier when locking-in the particular sample container 4 or micro-tube into the sample store 1.

The same reference numbers relate to the same features in the attached FIGS. 1-8, even when not in all cases these features are addressed in detail in the written disclosure of the specification. Now by way of an example, some dimensions are given for aspects of the disclosed embodiment of a modular sample store 1. These dimensions may vary according to the special requirements of a laboratory or building, the modular sample store is to be placed. In this exemplary embodiment is:

The length (in Y direction) of a vat module 11 2.35 m
The width (in X-direction) of a vat module 11 1.30 m
Thickness of the front and back wall plates 24,25 0.40 m
Thus, the footprint of the smallest modular sample store 1 (consisting of an interface unit 26 and one single functional segment 23 with a storage area 2) with these exemplary vat modules 11 measures 3.40 m×2.35 m.

For an exemplary temperature controlled low temperature sample store 1, which provides a storage temperature of −80° C. and a transfer area temperature of −20° C., the following dimensions of the clearance 19 (essentially filled with polymer foam material 20) between the outside and inside liners 17,18 are preferred:

Vat floor 14 (see FIGS. 2,3): 150 mm
Vat longitudinal wall 41 (see FIG. 2): 75 mm
Vat wall 15 (see FIGS. 3,5A): 125 mm
Vat side wall 35 (see FIG. 3,5B): 125 mm
Vat upper side wall 12 (see FIG. 3): 150 mm
Cover plate 13 (see FIG. 3): 100 mm.

A single storage stack 3 may have the following dimensions:

Total height in Z-direction: 795 mm
Length of the insulating cover 69 in Y-direction: 155 mm
Width of the insulating cover 69 in Y-direction: 98 mm.

Given the above dimensions of a modular sample store 1 and the exemplary dimensions of a storage stack 4, the maximum number of stacks in this exemplary modular sample store 1 is 110 (see FIGS. 2 and 3). In consequence, the maximum storage capacity of this exemplary modular sample store 1 is for:

Standard 96 deep well microplates: 1320
Standard 96 half deep well microplates: 2310
Standard 384 well microplates: 2860.

It is expressly pointed to the fact that when using insulating covers 69 for thermally isolating the storage area 2 from the transfer area 6, there may be is an air gap of about 1 mm between the adjacent individual insulating covers 69.

Each addition of a storage vat module 11 to the modular sample store 1 will add the above numbers to an already existing sample store 1. So, if 5 storage vat modules 11 are combined with an interface unit 26, a total number of e.g. 11'550 standard 96 half deep well microplates or 14'300 standard 384 well microplates can be stored in a sample store with a footprint of 8.60 m×2.35 m.

One aspect of the disclosed embodiment is to provide an alternate storage system that has been introduced at the beginning and that removes or at least minimizes the drawbacks known from the prior art.

One additional aspect of the disclosed embodiment is to provide an alternate low temperature storage system that removes or at least minimizes the drawbacks known from the prior art.

One further aspect of the disclosed embodiment is to provide a storage system that can be assembled on a customer's site more easily.

One more aspect of the disclosed embodiment is to provide a storage system that easily can be modified into a larger or smaller storage system on a customer's site.

The basis for reaching all the aspects of the disclosed embodiment, with respect to an alternate storage system that has been introduced at the beginning, is an integrally formed cubic vat module. In the smallest functional embodiment, the sample store storage area and the sample store service area each comprises one such vat module with an essentially horizontal vat floor and four joining vat walls that are connected to the vat floor and that are leaving an open vat space. The sample store also comprises upper side walls and a cover plate to close the sample store. Each vat floor and vat wall comprises an outside liner and an inside liner, which outside and inside liners in each case are separated by a clearance essentially being filled with a polymer foam material. This polymer foam material in its cured state provides fixation of the outside and inside liners to each other as well as thermal insulation of and reinforcement to the thus integrally formed cubic vat module sandwich construction.

Additional features according to aspects of the disclosed embodiment are described above.

Advantages of a sample store according to aspects of the disclosed embodiment include:

1. The elements of a sample store, such as vat module, upper side walls, and cover plate can be prefabricated, assembled and tested at the manufacturer's site, disassembled, transported by standard transportation vehicles and through standard laboratory doors, and easily assembled at the customer's site.

2. The storage vat module comprises all necessary equipment for full function of the sample storage area. Thus, adding a set of elements like storage vat module, upper side walls, and cover plate together with the necessary accessories, like ventilators and deep cooling devices, will double the storage capacity of the smallest working sample store.

3. Because of equipping each storage vat module with all necessary accessories, each storage vat module can be operated at an individual temperature in the temperature range of +25° C. to −90° C.

4. Because of equipping each storage vat module with all necessary accessories, an existing low temperature store can be extended by adding additional storage vat modules while the existing low temperature store continuously is in operation.

5. Functionally disconnecting accessories, like ventilators and deep cooling devices from the storage vat modules allows full servicing of these accessories without being obliged to thaw and empty a storage vat module.

6. The modular sample store provides high storage density in a compact housing of very small foot print.

7. Full functionality of the motorized robot is provided when up-scaling as well as when down-scaling a modular sample store.

In accordance with one or more aspects of the disclosed embodiment a modular sample store is provided and includes a storage area for taking up a number of storage stacks, which are accomplished for being inserted in an essentially vertical direction and for storing sample containers therein; a service area that is located adjacent to the storage area; a transfer area that is located above the storage area and the service area; a motorized robot that is located in the transfer area and that is movable in at least one essentially horizontal direction, the robot comprising a lifting device for lifting storage stacks at least partially out of the storage area and into the transfer area and for lowering storage stacks into the storage area; and ii) at least one platform for transporting at least one sample container within the transfer area; and a controller for controlling all actions and movements of the motorized robot, wherein the sample store service area comprises one integrally formed cubic vat module and the sample store storage area comprises at least one integrally formed cubic vat module, each one of said vat modules comprising an essentially horizontal vat floor and four joining vat walls that are connected to the vat floor and that are leaving an open vat space; wherein the modular sample store also comprises upper side walls and a cover plate to close the sample store; and wherein each vat floor and vat wall comprises an outside liner and an inside liner, which outside and inside liners in each case are separated by a clearance essentially being filled with a polymer foam material that provides fixation of the outside and inside liners to each other as well as thermal insulation of and reinforcement to the thus integrally formed cubic vat module sandwich construction.

In accordance with one or more aspects of the disclosed embodiment the integrally formed cubic vat module(s) of the storage area and the service area have the same size.

In accordance with one or more aspects of the disclosed embodiment each integrally formed cubic vat module is equipped with two upper side wall plates and one cover plate that have the same length as one of the vat modules so as to form a functional segment of the modular sample store, and wherein the sample store also comprises a front wall plate and a back wall plate to close the sample store.

In accordance with one or more aspects of the disclosed embodiment the sample store also comprises a number of storage stacks that are inserted in an essentially vertical direction into the open vat space of one of the vat modules in the storage area and that are accomplished for storing sample containers in an essentially horizontal position therein.

In accordance with one or more aspects of the disclosed embodiment the sample store also comprises an interface unit that is located in a part of the transfer area, which is situated over the service area and that comprises the service area and a lock, which is accomplished for locking-in sample containers into the sample store and for locking-out sample containers out of the sample store, wherein the robot is implemented for transporting at least one sample container to and from the interface unit.

In accordance with one or more aspects of the disclosed embodiment the sample store is accomplished as a temperature controlled modular sample store and comprises at least one temperature control device for circulating the air in the service area and in the transfer area of the sample store (1) and for controlling the air temperature to at most +25° C., preferably to at most +4° C., and more preferably to at most −20° C., said at least one temperature control device preferably being located in working connection with an interface unit, In accordance with one or more aspects of the disclosed embodiment each integrally formed cubic vat module of the storage area of the sample store comprises a first air outlet opening and a first air inlet opening located in a vat side wall, to which first air outlet opening is connected a ventilator for circulating the temperature controlled air in the integrally formed cubic vat module of the storage area.

In accordance with one or more aspects of the disclosed embodiment the sample store is accomplished as a temperature controlled low temperature modular sample store and comprises at least one cooling device for cooling and controlling the air temperature to at most −20° C. and for circulating the cooled air in the service area and in the transfer area of the sample store, said at least one cooling device being located in working connection with an interface unit.

In accordance with one or more aspects of the disclosed embodiment each integrally formed cubic vat module of the storage area of the sample store comprises at least one deep cooling device for deep cooling the air to a temperature of at least −80° C. and at least one ventilator that are connected to one first air outlet opening and to one first air inlet opening located in a vat side wall for circulating the deep cooled air in the integrally formed cubic vat module of the storage area of the sample store.

In accordance with one or more aspects of the disclosed embodiment the at least one deep cooling device and one ventilator are accommodated in one common housing, which is located outside the vat module, and which is in working connection with each one of the vat modules via said first air outlet and inlet openings located in each one of the vat side walls.

In accordance with one or more aspects of the disclosed embodiment each one of the integrally formed cubic vat modules of the storage area of the sample store comprises at least one individual first deep cooling device and at least one individual ventilator that are accommodated in one common housing, which is located at the vat side wall outside the vat module (11), and which is in working connection with the vat module (11) via said first air outlet and inlet openings (32,39).

In accordance with one or more aspects of the disclosed embodiment each integrally formed cubic vat module of the storage area comprises second air outlet and inlet openings situated in the vat side wall, to which second air outlet and inlet openings is connected an individual second deep cooling device, which is located in a separate housing at the vat side wall outside the vat modules.

In accordance with one or more aspects of the disclosed embodiment each one of said first and second air outlet openings and each one of said first and second air inlet openings is equipped with a shutter for closing the respective openings and thus separating one of a ventilator, a combination of a first deep cooling device and a ventilator, and a combination of a second deep cooling device and a ventilator from the integrally formed cubic vat module of the storage area of the sample store to which said openings guide.

In accordance with one or more aspects of the disclosed embodiment each vat module of the storage area also comprises an air out channel and an air in channel that are situated at the inside of the vat side wall and that mouth to inner openings, which lead to the vat space of each vat module of the storage area; the air out channel being connected to the air outlet openings and the air in channel being connected to the air inlet openings.

In accordance with one or more aspects of the disclosed embodiment each one of said inner openings is located close to a longitudinal vat wall that join said vat side wall, and wherein two air guiding blades with ventilation holes are positioned in a distance to one or the other of the longitudinal vat walls for distributing deep cooled air to or collecting deep cooled air form the vat space.

In accordance with one or more aspects of the disclosed embodiment each construction part selected from the group comprising the integrally formed cubic vat modules, the upper side walls, and the cover plates has mechanical connecting elements for reversibly connecting two of these construction parts mutually.

In accordance with one or more aspects of the disclosed embodiment each integrally formed cubic vat module of the storage area and of the service area comprises carrying structures on the vat side walls and vat longitudinal walls, which carrying structures support horizontal rails for moving the robot in an X-direction.

In accordance with one or more aspects of the disclosed embodiment the motorized robot comprises an insulated hood that is located in the transfer area, the robot, when using the lifting device, being capable to lift an entire storage stack out of its original vat space and into said insulated hood, to transport the storage stack inside of said insulated hood within the transfer area, and to lower the storage stack into a deep cooled vat space of another integrally formed cubic vat module of the sample store storage area.

In accordance with one or more aspects of the disclosed embodiment the motorized robot comprises an insulated hood that is located in the transfer area, the robot, when using the lifting device, being capable to partially lift a storage stack into said insulated hood and up to a level, which is accessible by a spatula of the robot; the spatula being accomplished to be moved into the insulated hood and below a certain sample container; the robot being accomplished to move said certain sample container out of the storage stack in horizontal direction and to move this or another sample container into the storage stack in horizontal direction.

In accordance with one or more aspects of the disclosed embodiment the motorized robot is lacking an insulated hood and when using the lifting device, is capable of partially lifting a storage stack) up to a level, which is accessible by a spatula of the robot; the spatula being accomplished to be moved into the storage stack and below a certain sample container; the robot being accomplished to move said certain sample container out of the storage stack in horizontal direction and to move this or another sample container into the storage stack in horizontal direction.

In accordance with one or more aspects of the disclosed embodiment the sample container is one of a multi-well microplate, a blood bag, a cell culture flask, and a microplate-sized micro-tube rack.

In accordance with one or more aspects of the disclosed embodiment the robot further comprises a Z-module for lifting a sample container in the form of a microplate-sized micro-tube rack from the spatula in a vertical Z-direction and for setting said sample container onto a first carrier or onto a second carrier of the platform of the robot, both carriers (being individually moveable in a horizontal X-direction and in a horizontal Y-direction perpendicular to the X-direction.

In accordance with one or more aspects of the disclosed embodiment the robot comprises a punching device for pushing a micro-tube out of a compartment of a first microplate-sized micro-tube rack or source plate into a compartment of a second microplate-sized micro-tube rack or destination plate.

In accordance with one or more aspects of the disclosed embodiment the source plate is located above the destination plate, the punching device pushing down a micro-tube in vertical Z-direction.

In accordance with one or more aspects of the disclosed embodiment each integrally formed cubic vat module of the sample store storage area comprises a guiding grid that is located in the vat space (16), that is supported by guiding posts standing on the vat floor, and that defines an array of apertures adapted to the size of storage stacks, each of which storage stacks being vertically movable in one of these apertures; the guiding posts partly engaging slide grooves (63) located on two opposite vertical sides of the storage stacks (3) and guiding vertical movement of the storage stacks.

In accordance with one or more aspects of the disclosed embodiment the storage stacks comprise lateral support flanges with carrying webs that carry the weight of a storage stack when it is lowered to its lowermost position in the vat space, the carrying webs of the lateral support flanges being supported by the guiding grid.

In accordance with one or more aspects of the disclosed embodiment the storage stacks comprise an individual trunnion at their lower end, said trunnion carrying the weight of a storage stack when it is lowered to its lowermost position in the vat space by abutting the vat floor.

In accordance with one or more aspects of the disclosed embodiment each storage stack comprises at its upper end a carrying element that is engageable by the lifting device and that is attached to a carrying structure with lateral support flanges equipped with mutual storage webs for supporting one sample container on top of the other and in a horizontal position.

In accordance with one or more aspects of the disclosed embodiment each storage stack comprises an individual insulating cover at its upper end, the carrying element being located in a depression on the upper side of the individual isolating cover.

In accordance with one or more aspects of the disclosed embodiment each storage stack comprises surfaces to which is applied an anti-frost coating.

In accordance with one more aspects of the disclosed embodiment, a storage method for storing and providing samples in a modular sample store is provided. The method includes storing samples in a storage area for taking up a number of storage stacks, which are accomplished for being inserted in an essentially vertical direction and for storing sample containers therein; providing a service area that is located adjacent to the storage area; providing a transfer area that is located above the storage area and the service area; Providing a motorized robot that is located in the transfer area and that is movable in at least one essentially horizontal direction, the robot comprising: a lifting device for lifting storage stacks at least partially out of the storage area and into the transfer area and for lowering storage stacks into the storage area; and at least one platform for transporting at least one sample container within the transfer area; and controlling all actions and movements of the motorized robot with a controller, wherein the sample store service area is provided with one integrally formed cubic vat module and the sample store storage area is provided with at least one integrally formed cubic vat module, each one of said vat modules comprising an essentially horizontal vat floor and four joining vat walls that are connected to the vat floor and that are leaving an open vat space; wherein the modular sample store is closed by also providing upper side walls and a cover plate; and wherein each vat floor and vat wall that comprises an outside liner and an inside liner, which outside and inside liners in each case are separated by a clearance, is essentially filled with a polymer foam material so that fixation of the outside and inside liners to each other as well as thermal insulation of and reinforcement to the thus integrally formed cubic vat module sandwich construction is provided.

In accordance with one or more aspects of the disclosed embodiment storing of a sample includes identifying and inserting a sample container via a lock into an interface unit of the sample store; moving the sample container with the robot to a selected storage stack with an empty storage position and positioning the sample container on a spatula; lifting the selected storage stack by the lifting device of the robot to a level that the empty storage position of the storage stack is reachable by the sample container positioned on the spatula; inserting into the empty storage position of the storage stack the spatula with the sample container positioned thereon; lowering the storage stack for an incremental distance to place the sample container on mutual storage webs of lateral support flanges of the storage stack; withdrawing the spatula from the storage stack; and lowering the storage stack to its lowermost position in the vat space of the integrally formed cubic vat module of the sample store storage area.

In accordance with one or more aspects of the disclosed embodiment identifying a sample container includes reading of a machine readable identifier of the sample container; reading of additional information provided by the machine readable identifier; and measuring the average temperature of the sample container.

In accordance with one or more aspects of the disclosed embodiment the selected storage stack with an empty storage position is chosen by the controller according to at least one of the identifier of the sample container; the additional information provided; and the average temperature of the sample container; and wherein the selected storage stack with an empty storage position is a pre-in/out storage stack or a permanent storage stack.

In accordance with one or more aspects of the disclosed embodiment storing of a sample comprises keeping the air in the storage, service, and transfer areas of the sample store at a temperature in the range from +25° C. to −20° C.

In accordance with one or more aspects of the disclosed embodiment storing of a sample comprises keeping the air in the storage area at a temperature in the range from −20° C. to −90° C. and keeping the air in the service and transfer areas at a temperature of −20° C.

In accordance with one or more aspects of the disclosed embodiment one or more pre-in/out stacks are provided within the integrally formed cubic vat module of the storage area, which is located adjacent to the integrally formed cubic vat module of the service area, and wherein the interface unit of the sample store that comprises the lock is located in that part of the transfer area of the sample store that is located above and that comprises the service area.

In accordance with one or more aspects of the disclosed embodiment the temperature of the cooled air within the vat space of the integrally formed cubic vat module that contains the pre-in/out stacks is kept at a temperature lower than −80° C., preferably at −90° C., for compensating heat input by sample containers arriving from the lock.

In accordance with one or more aspects of the disclosed embodiment the motorized robot controlled by the controller inserts sample containers into storage stacks or withdraws sample containers from storage stacks according to a certain job request.

In accordance with one or more aspects of the disclosed embodiment the controller forces the motorized robot to interrupt a requested job, if the longest allowable presence of one of the sample containers or micro-tubes in that sample container has reached a limit that has been set according to additional information, which has been provided by the machine readable identifier when locking-in the particular sample container or micro-tube into the modular sample store.

LIST OF REFERENCE NUMBERS 1 sample store
2 storage area
3 storage stack
4 sample container
5 service area
6 transfer area
7 motorized robot
8 lifting device
9 platform
10 controller
11 vat module
12 upper side walls, side wall plate
13 cover, cover plate
14 vat floor
15 vat wall
16 vat space
17 outside liner
18 inside liner
19 clearance
20 polymer foam material
21 multiplex plate
22 stainless steel sheet
23 functional segment
24 front wall plate
25 back wall plate
26 interface unit
27 lock
28 temperature control device
29 ventilator
30 cooling device
31 first deep cooling device
32 first air outlet opening
33 second deep cooling device
34 second air outlet opening
35 vat side wall
36 common housing
37 separate housing
38 shutter
39 first air inlet opening
40 second air inlet opening
41 longitudinal vat wall
42 air out channel
43 air in channel
44 inner opening
45 air guiding blade
46 venting holes
47 distance
48 mechanical connecting elements
49 carrying structures
50 horizontal rails
51 insulated hood
52 spatula
53 Z-module
54 first carrier
55 second carrier
56 punching device
57 compartment
58 source plate
59 destination plate
60 guiding grid
61 guiding posts 62 apertures
63 slide grooves
64 lateral support flanges
65 individual trunnion
66 carrying element
67 carrying means
68 mutual storage webs
69 Individual insulating cover
70 Depression
71 anti-frost coating
72 door
73 workstation
74 orientation pin
75 punching element
76 micro-tube
77 in/out stack
78 single plate interface
79 conveyor belt
80 deep cooling aggregate
81 evaporator

The invention claimed is:

1. A modular sample store comprising:
 storage stacks;
 a storage area configured for storing the storage stacks, each storage stack holding at least one sample container;
 a transfer area located above the storage area; and
 a motorized robot located in the transfer area, the motorized robot including a picker, an insulated hood and a lifting device, the lifting device being configured to at least partially lift a predetermined one of the storage stacks into the insulated hood from the storage area and up to a position which is accessible by the picker,
 wherein the motorized robot is configured to,
  place the picker into the insulated hood,
  engage a selected sample container in the predetermined storage stack with the picker, and
  move the picker to remove the selected sample container of the predetermined storage stack from the insulated hood.

2. The modular sample store of claim 1, wherein the motorized robot is further configured to lower the predetermined storage stack back into the storage area.

3. The modular sample store of claim 1, wherein the motorized robot positions the picker below the selected sample container to engage the selected sample container.

4. The modular sample store of claim 3, wherein the motorized robot incrementally lowers the storage stack with the lifting device so that the selected sample container is placed upon the picker.

5. The modular sample store of claim 1, wherein the motorized robot places the picker into the insulated hood in a first direction to engage the selected sample container and moves the picker in a second direction opposite the first direction to remove the selected sample container.

6. The modular sample store of claim 1, wherein the motorized robot further comprises a platform having a carrier.

7. The modular sample store of claim 1, wherein the motorized robot further comprises a sample container lifting module configured to lift the selected sample container from the picker.

8. A method for storing and providing samples, comprising:
 lifting a predetermined storage stack into an insulated hood with a lifting device of a motorized robot to a position where a selected sample container of the predetermined storage stack is accessible by a picker of the motorized robot;
 placing the picker into the insulated hood,
 engaging the selected sample container with the picker; and
 moving the picker to remove the selected sample container of the predetermined storage stack from the insulated hood.

9. The method for storing and providing samples of claim 8, wherein the method further comprises lowering the storage stack to its lowermost position with the lifting device into a sample store storage area.

10. The method for storing and providing samples of claim 8, further comprising positioning the picker below the selected sample container to engage the selected sample container.

11. The method for storing and providing samples of claim 10, wherein the method further comprises incrementally lowering the predetermined storage stack with the lifting device so that the selected sample container is placed upon the picker.

12. The method for storing and providing samples of claim 8, further comprising placing the picker into the insulated hood in a first direction to engage the selected sample container and moving the picker in a second direction opposite the first direction to remove the selected sample container.

* * * * *